US005925546A

United States Patent [19]

Pizza et al.

[11] Patent Number: 5,925,546

[45] Date of Patent: Jul. 20, 1999

[54] IMMUNOLOGICALLY ACTIVE POLYPEPTIDES WITH ALTERED TOXICITY USEFUL FOR THE PREPARATION OF AN ANTIPERTUSSIS VACCINE

[75] Inventors: Mariagrazia Pizza; Antonella Bartoloni; Rino Rappuoli, all of Siena, Italy

[73] Assignee: Chiron S.p.A., Siena, Italy

[21] Appl. No.: 08/478,714

[22] Filed: Jun. 7, 1995

Related U.S. Application Data

[62] Division of application No. 08/261,692, Jun. 17, 1994, which is a continuation of application No. 07/968,381, Oct. 29, 1992, abandoned, which is a continuation of application No. 07/265,742, Nov. 1, 1988, abandoned.

[30] Foreign Application Priority Data

Nov. 2, 1987 [IT] Italy .................................... 2248A-87

[51] Int. Cl.[6] ............................ C12P 21/02; C12N 15/00

[52] U.S. Cl. .................... 435/69.3; 435/320.1; 536/23.7; 424/190.1; 424/254.1; 424/832

[58] Field of Search ......................... 530/350; 424/240.1, 424/190.1, 254.1, 832; 435/69.1, 69.3, 172.3, 320.1; 536/23.7

[56] References Cited

U.S. PATENT DOCUMENTS

| | | | |
|---|---|---|---|
| 5,085,862 | 2/1992 | Klein et al. | 424/197.1 |
| 5,221,618 | 6/1993 | Klein et al. | 435/69.1 |
| 5,244,657 | 9/1993 | Klein et al. | 424/190.1 |
| 5,332,583 | 7/1994 | Klein et al. | 424/190.1 |
| 5,358,868 | 10/1994 | Klein et al. | 435/69.1 |
| 5,433,945 | 7/1995 | Klein et al. | 424/185.1 |
| 5,773,600 | 6/1998 | Burnette | 536/23.7 |

OTHER PUBLICATIONS

Black, W.J. et al., Non–toxigenic Mutants of "*Bordetella Pertussis*", *Ann. Scalvo* 1986, N. 1–2, pp. 175–182, Proceedings of Scalvo International Conference, Siena, Italy, Nov. 17–19, 1986.

Bowie, J. et al., "Deciphering the Message in Protein Sequences: Tolerance to Amino Acid Substitutions", *Science* 1990, 247, 1306–1310.

Kumar, V. et al., "Amino Acid Variations at a Single Residue in an Autoimmune Peptide Profoundly Affects its Properties: T–cell Activation, Major Histocompatibility Complex Binding, and Ability to Block Experimental Allergic Encephalomyelitis", *PNAS USA* 1990, 87, 1337–1341.

Nicosia, A. et al., "Expression and Immunological Properties of the Five Subunits of Pertussis Toxin", *Infection and Immunity* 1987, 55(4), 963–967.

Pizza, M. et al., "Mutants of Pertussis Toxin Suitable for Vaccine Development", *Science* 1989, 246, 497–500.

Stibitz, S. et al., "The Construction of a Cloning Vector Designed for Gene Replacement in *Bordetella pertussis", Gene* 1986, 50, 133–140.

Nicosia, A. et al. Apr. 1987. "Expression and immunological properties of the five subunits of pertussis toxin." Infection and Immunity, vol. 55, pp. 963–967.

Nicosia, A. et al. Jul. 1986. "Cloning and sequencing of the pertussis toxin genes: operon structure and gene duplication." Proceedings of the National Academy of Sciences, vol. 83, pp. 4631–4635.

Locht, C. et al. Nov. 1987. "Activities of complete and truncated forms of pertussis toxin subunits S1 and S2 synthesized by *Escherichia coli*." Infection and Immunity, vol. 55, pp. 2546–2553.

Rappuoli, R. et al. 1987. "Pertussis toxin." Chimicaoggi–maggio 1987, pp. 46–48.

Black, W.J. et al. Oct. 1987. "Construction and characterization of *Bordetella pertussis* toxin mutants." Infection and Immunity, vol. 55, pp. 2465–2470.

Pizza, M.G. et al. 1990. Pertussis toxin CRMs and new vaccines against whooping cough. In: Rappuoli et al, Bacterial Protein Toxins, Zbl. Bakt. Suppl. 19, pp. 507–518.

*Primary Examiner*—Mary E. Mosher
*Attorney, Agent, or Firm*—Woodcock, Washburn, et al.; Alisa A. Harbin; Robert P. Blackburn

[57] ABSTRACT

Immunological active polypeptides with no or reduced toxicity useful for the preparation of an antipertussis vaccine. Method for the preparation of said polypeptides which comprises, cultivating a microorganism transformed with a hybrid plasmid including the gene/s which codes for at least one of said polypeptides in a suitable medium and recovering the desired polypeptide from the cells or from the culture medium.

5 Claims, No Drawings

IMMUNOLOGICALLY ACTIVE POLYPEPTIDES WITH ALTERED TOXICITY USEFUL FOR THE PREPARATION OF AN ANTIPERTUSSIS VACCINE

This application is a divisional of applicants' application Ser. No. 08/261,692, filed Jun. 17, 1994, which is a continuation of Ser. No. 07,968,381, filed Oct. 29, 1992 now abandoned, which is a continuation of Ser. No. 07,265,742, filed Nov. 1, 1998, now abandoned, which claims priority benefit under 35 USC §119 of applicants' Italian application Ser. No. 2248/A87, filed Nov. 2, 1987.

DESCRIPTION

The present invention relates to immunologically active polypeptides with no or reduced toxicity useful for the production of an antipertussis vaccine.

The invention also relates to a method for the preparation of said polypeptides and to an antipertussis vaccine comprising a therapeutically effective amount of at Least one of said polypeptides.

Pertussis is a respiratory system disease caused by *Bordetella pertussis* (*B. pertussis*), a bacillus the transmission of which occurs during the catarrhal and convulsive phase from a sick person to a healthy predisposed individual through the respiratory system.

A vaccine effective against said disease is particularly desirable since pertussis may cause convulsions, cerebral damages and, sometimes, death, principally in tender age children and in newborn babies lacking maternal antipertussis antibodies obtained passively.

At present, it is employed an antipertussis vaccine comprising virulent bacteria killed with merthiolate and treated at 56° C. that, even if it confers a permanent protection, it is not, however, completely satisfactory, either for the presence of undesired side effects or for the numerous problems deriving from the preparation and purification thereof.

This results in the necessity of preparing an antipertussis vaccine lacking of the aforementioned drawbacks.

It is known that *B. pertussis* has, per se, no virulence and that its toxicity is correlated with the synthesis, during the phase I (virulent), of such substances as: hemolysin (HLs), adenylcyclase (Adc), dermonecrotic toxin (Dnc), filamentary hemagglutinin (Fha) and pertussis toxin (PT). The latter, in particular, represents not only the major virulence factor caused by *B. pertussis* (Weiss A. et al. (1983) Infect, Immun. 42, 333–41; Weiss A. et al. (1984) J. Inf. Dis. 150, 219–222) but also one of the major protective antigens against infections caused by said bacterium.

Anti-PT antibodies, in fact, have been found in individuals immunized by the cellular vaccine (Ashworth L. A. E. et al. (1983) Lancet. Oct. 878–881) and a protective immunity has been obtained in mice infected, via aerosol or intracerebrally, using formaldehyde-detoxified PT (Sato Y. et al. (1983) Inf. and Imm. 41, 313). Even if the pertussis toxin represents an essential component in the preparation of new antipertussis vaccines, its use is Limited by the numerous drawbacks deriving from its toxicity.

The PT, in fact, induces undesirable pathophysiologic effects such as: lymphocytosis, histamine sensitivity, hypoglycemia, insensitivity to the hyperglycemic effect of epinephrine and activation of the islands of Langerhans.

Furthermore, it has been found that the PT presence in the vaccine now employed is the principal cause of such side effects as: fever, pomphus, neurologic alteration and death which have led, in recent years, to drastically reducing the use of the vaccine with the consequent new outbreak of pertussis cases.

The PT detoxification treatment by means of formaldehyde though allowing to get an immunogenic protein without toxicity (Sato et al. reference reported above), presents some drawbacks deriving from the fact that said protein is not obtainable in pure, reproducible and stable form. According to that, polypeptides have now been found which are able to overcome the prior art drawbacks and are obtainable in pure form by means of a simple and economically feasible method. One object of the present invention, therefore, consists of immunologically active polypeptides with no or reduced toxicity useful for the preparation of an antipertussis vaccine.

A further object of the present invention consists of a method for the preparation of said polypeptides.

Another object of the present invention is a vaccine comprising a therapeutically effective amount of at least one of said polypeptides.

Further objects of the present invention will become apparent from a reading of the following description and examples.

The pertussis toxin is a protein comprising five different subunits the toxicity of which is due to ADP-ribosylation of proteins which bind GTP involved in the transmission of messages through eukaryotic cells membranes.

Said PT comprises two fractions with different functionality: A comprising the S1 subunit and B comprising S2, S3, S4 and S5 subunits placed in two dimers D1 (S2+S4) and D2 (S3+S4) linked to each other by the S5 subunit.

The A fraction represents the enzymatically active and therefore toxic part of PT, whereas the B fraction is linked to the eukaryotic cells membrane receptors and allows the introduction of the S1 subunit therein.

In the copending Italian patent application No. 19208-A/86, now filed in the United States as U.S. application Ser. No. 07/006,438, filed Jan. 23, 1987, the cloning, sequencing and expression of the genes which code for said subunits have been described and claimed and it has been shown that said genes are grouped in a sole operon.

Furthermore, the ADP-ribosylation activity of the S1 subunit has been determined, by cultivating a microorganism transformed with the hybrid plasmid PTE225, and it has been found that said subunit possesses an enzymatic activity comparable to that of PT.

According to that and to the end of obtaining a protein having the immunologic and protective properties of the pertussis toxin but with no or reduced toxicity, the positions and the fundamental aminoacids for the enzymatic activity of the protein have been identified. In particular, the following positions and amino acids have been found:

tyrosine (8), arginine(9), phenylalanine (50),threonine (53), glutamic acid (129), glycine (121), alanine (124), aspartic acid (109), glycine (99), arginine (135), threonine (159) and tyrosine (111).

The substitution of one or more of said aminoacids with any aminoacid different from the one which is bound to be changed, allows to obtain a protein with altered toxicity.

According to that, in accordance with the present invention, polypeptides have been synthetized containing S1 subunits of the modified pertussis toxin by means of direct mutagenesis substituting, in one or more positions of the S1 region comprised between the 1–80 aminoacids, one aminoacid with another capable of destroying or reducing its enzymatic activity without altering the immunologic properties thereof.

In particular, polypeptides have been synthetized containing the S1 subunit of the pertussis toxin modified by substituting:

the tyrosine in position 8 and arginine in position 9 with aspartic acid and glycine;

the phenylalanine in position 50 and the threonine in position 53 with glutamic acid and isoleucine;

the glutamic acid in position 129 with glycine;

the glycine in position 121 with glutamic acid;

the alanine in position 124 with aspartic acid;

the aspartic acid in position 109 and the alanine in position 124 with glycine and aspartic acid respectively;

the glycine in position 99 with glutamic acid;

the aspartic acid in position 109 with glycine;

the arginine in position 135 with glutamic acid;

the threonine in position 159 with lysine;

the tyrosine in position 111 with glycine and insertion of Asp Thr Gly Gly amminoacids in position 113.

In particular, the polypeptides according to the present invention have been prepared by a method which comprises:

a) modifying by means of direct mutagenesis the gene which codes for the S1 subunit of the pertussis toxin substituting, in one or more sites of the DNA molecule, the bases sequence which codes for a predetermined aminoacid with a bases sequence which codes for the aminoacid of interest;

b) constructing a hybrid plasmid linking a cloning vector with the DNA fragment containing the modified S1;

c) transforming a host microorganism with a hybrid plasmid obtained as reported in b);

d) cultivating in a suitable culture medium, in presence of carbon, nitrogen and mineral salts sources a transformed microorganism and then, e) recovering the polypeptide containing the modified S1 subunit from the culture medium or from the cells.

According to the present invention and to the end of identifying the S1 aminoacidic region correlated to the enzymatic activity of the protein, the gene which codes for S1 has been treated with restriction enzymes that cut in different sites and the DNA .fragments so obtained, lacking of the 3' and/or 5' of different length terminal sequences, have been cloned in an espression plasmid operating according to one of the generally known techniques The vectors containing the DNA fragments with the deleted sequences have been then employed to transform *Escherichia coli* (*E. coli*) cells.

The positive transformants, obtained screening the cells on a selective medium, have been cultivated in a suitable culture medium at temperatures between 30° C. and 40° C. for a period of from 20 minutes to 5 hours.

At the end of said period, the cells have been recovered from the culture medium and lysed by means of lysozym treatment and sonication.

The proteins so extracted have been analyzed to determine the presence of an enzymatic activity.

In practice the ADP-ribosylation activity of said proteins has been tested operating according to the method described by Manning et al. (1984) (J. Biol. Chem. 259, 749–756). The results obtained, Listed in table I of the following example 2, show that S1 sequences following the aminoacid in position 179, are not necessary for the ADP-ribosylation activity, unlike the first ten aminoacids.

The enzymatically active region of the S1 subunit, therefore, is comprised between the 1 and 180 aminoacids. According to that, in accordance with the present invention, the identification of the active sites present in said region has been performed and at least one of said sites has been modified.

In practice, the gene coding for S1 has been isolated from the PTE 255 plasmid, the construction of which is reported in the copending Italian patent application No. 19208-A/86, by means of digestion with the restriction enzymes EcoRI and HindIII.

The 600 base pairs DNA fragment, comprising the gene coding for S1, has been separated from the digestion mixture by means of gel electrophoresis and, after electro-elution, has been modified by direct mutagenesis which allows to introduce in vitro mutations in determined sites of a DNA molecule and to test in vitro or in vivo the effect of said mutation.

By this method the substitution of the desired base it is made possible operating in one of the following ways:

by incorporating base analogues in DNA sites;

by incorporating in a wrong way nucleotides;

by introducing the mutation during the synthesis in vitro of oligonucleotides with definite sequences;

by using specific chemical mutagen agents, such as sodium bisulfite, which react with the DNA bases.

According to the present invention, the gene coding for S1 has been modified by using synthetic oligonucleotides with definite sequences operating according to the method described by Zoller M. J. et al. (DNA 3:479–488, (1984)).

In practice, the 600 bp DNA fragment has been cloned in a vector which allows the isolation of the single helix clone fragment of the DNA.

To this end, suitable vectors may be selected from Bluescript SK (Stratagene S. Diego, Calif.), pEMBL (Dente et al. Nucleic Acids Research 11, 1645–1655 (1983) or M13 phages (Vierra and Messing (1982) Gene, 12, 263).

According to the present invention the commercially available Bluescript SK vector has been employed.

Said vector has been treated with suitable restriction enzymes and then Linked to the 600 bp DNA fragment in ligase mixture in presence of the T4 DNA Ligase enzyme.

The mixture has been then employed to transform *E. coli* cells and the transformants have been successively selected on a culture medium including ampicillin.

The positive clones, containing the hybrid plasmids comprising the vector and the 600 bp DNA fragment, have been suspended in a liquid medium in the presence of phages and maintained at a temperature of from 30° C. to 40° C. for a period of from 2 to 10 hours.

At the end of said period, the phages have been precipitated, separated from the solution by centrifugation, resuspended in a pH 7.5 buffer, extracted with water-ethyl ether saturated phenol and then extracted with ethanol and ammonium acetate in order to precipitate the single helix DNA.

Aliquots of said DNA have then been employed to modify the S1 gene by direct mutagenesis. To this end oligonucleotides of about 20 nucleotides have been synthetized in which the bases which code for one or more aminoacids present in determined sites of the 1–180 S1 region have been substituted with others which code for a different aminoacid. In particular oligonucleotides have been synthetized which allow to prepare the following mutants of the gene coding for S1:

41: Tyrosine 8 and arginine 9 are substituted with Aspartic and Glycine respectively using the primer GTCATAGCCGTCTACGGT.

The corresponding gene has been modified in this way:

620-CGCCACCGTATACCGCTATGACTCCCGCCCG-650

620-CGCCACCGTAGACGGCTATGACTCCCGCCCG-650

22: Phenylalanine 50 and threonine 53 are substituted with glutamic acid and isoleucine respectively using the primer TGGAGACGTCAGCGCTGT.

The corresponding gene has been modified in this way:

The sequence 750-AGCGCTTTCGTCTCCACCAGC-770 has been changed into 750-AGCGCTGACGTCTCCATCAGC-770.

15: Glycine 99 has been substituted with glutamic acid using the primer CTGGCGGCTTCGTAGAAA.

The corresponding gene has been so modified:

the sequence 910-TACGGCGCCGC-920 has been changed into 910-TACGAAGCCGC-920.

17: Aspartic acid 109 has been substituted with glycine using the primer CTGGTAGGTGTCCAGCGCGCC.

The corresponding gene has been so modified:

the sequence 930-GTCGACACTTA-940 has been changed into 930-GTCGGCACTTA-940.

27: Glycine 121 has been substituted with glutamic acid using the primer GCCAGCGCTTCGGCGAGG.

The corresponding gene has been so modified:

the sequence 956-GCCGGCGCGCT-966 has been changed into 956-GCCGAAGCGCT-966.

16: Alanine in 124 position has been substituted with aspartic acid using the primer GCCATAAGTGCCGACGTATTC.

The corresponding gene has been so modified:

the sequence 976-TGGCCACCTAC-984 has been changed into 976-TGGACACCTAC-986.

1716: contains the combined 16 and 17 mutations.

28: Glutamic acid 129 has been substituted in glycine using the primer GCCAGATACCCGCTCGG.

The corresponding gene has been so modified:

the sequence 990-AGCGAATATCT-1000 has been changed into 990-AGCGGGTATCT-1000.

29: Arginine 135 has been substituted with glutamic acid using the primer GCGGAATGTCCCGGTGTG.

The corresponding gene has been so modified:

the sequence 1010-GCGCATTCCGC-1020 has been changed into 1010-GGACATTCCGC-1020.

31:Threonine 159 has been substituted with lysine using the primer TACTCCGTTTTCGTGGTC.

The corresponding gene has been so modified:

1070-GCATCACCGGCGAGACCACGACCACGGAGTA-1090 has been changed into 1070-GCATCACCGGCGAGACCACGAAAACGGAGTA-1090.

26: Tyrosine 111 is substituted with glycine.

Furthermore, owing to a partial duplication of a primer fragment, the insertion of the Asp Thr Gly Gly aminoacids occurred in position 113 using the primer CGCCACCAGTGTCGACGTATTCGA. The corresponding gene has been so modified:

930-GTCGACACTTATGGCGACAAT-950

930-GTCGACACTGGTGGCGACACTGGTGGCGACAAT-950.

Said oligonucleotides have been used as primers for DNA polymerase which transcribes all the nucleotidic sequence of the vector incorporating the mutations present in the primer.

The vectors containing the S1 gene with the desired modification have been isolated by the hybridization technique using as probe the primer itself.

The exact nucleotide sequence of the modified gene has been then confirmed by the technique of Sanger F. et al. (P.N.A.S. 74, 5463, 1977).

The vectors containing the modified genes have been then digested with the restriction enzymes EcoRI and HindIII and the DNA fragments containing the gene coding for the modified S1 have been cloned in an expression plasmid selected from those known in the art.

Said hybrid plasmids have been employed to transform a host microorganism selected among *E.coli, Bacillus subtilis* and yeasts.

In particular, according to the present invention, the plasmid PEx34(Center for Molecular Biology, Heidelberg, Federal Republic of Germany) and the microorganism *E.coli* K12-ΔHL-Δtrp (Remant, E. et al. Gene, 15, 81–93, 1981) have been employed.

The transformed microorganisms have been then cultivated in a Liquid culture medium in the presence of carbonium, nitrogen and mineral salt sources, at a temperature comprised between 30° C. and 45° C. for a period of from 20 minutes to 5 hours.

At the end of the period the cells have been recovered from the culture medium by centrifuging and lysed by means of generally known techniques.

The cellular lysates containing the proteins have been then analyzed to determine the enzymatic activity thereof.

The results, reported in the following example 3, show that a good reduction (5–80%) of the ADP-ribosylation activity and therefore of toxicity has been obtained by substituting in the S1 sequence the aminoacids in 109 (17) and 124 (16) positions, either separately or in combination, and the aminoacid in 121 position (27).

A complete loss of the S1 subunit enzymatic activity has been observed by substituting the aminoacids in the positions 8 and 9 (41), 50 and 53 (22) and 129 (28).

Furthermore, said subunits are able to induce in vivo specific antibodies and to react (subunit 28) with anti-PT protective monoclonal antibodies.

Polypeptides containing said modified subunits, therefore, are suitable for the preparation of an antipertussis vaccine.

Preferred are the polypeptides containing in addition to the modified S1 subunit at least one of the S2, S3, S4 and S5 PT subunits.

Particularly preferred are the polypeptides having said S2, S3, S4 and S5 subunits with the same arrangement and configuration presented by the antipertussis toxin.

Said preferred polypeptides may be prepared modifying the gene coding for S1 contained in the PT operon and constructing plasmids, comprising the whole operon with the modified S1 gene or regions thereof, which essentially code for a polypeptide containing the modified S1 subunit and one or more of the S2, S3, S4 and S5 subunits.

More specifically, said polypeptides are prepared by:

(a) modifying by direct mutagenesis the gene coding for the S1 subunit of the pertussis toxin substituting in one or more sites of the DNA molecule the base sequence which codes for a determined amino acid with a base sequence which codes for an amino acid of interest;

(b) constructing a hybrid plasmid linking a cloning vector with the DNA fragment containing the gene coding for the modified S1 subunit;

(c) transforming a host microorganism with a hybrid plasmid obtained as in (b);

(d) cultivating the transformed microorganism in a suitable culture medium in the presence of carbon, nitrogen and mineral salts sources; and finally (e) recovering the polypeptide containing the modified subunit from the culture medium of the cells. Preferably, the DNA fragment in step (b) contains at least one gene coding for the S2, S3, S4 and S5 subunits.

According to the present invention, the plasmids PTE 255-22, PTE 255-28 and PTE 255-41, containing the gene which codes for the S1 modified subunits 22, 28 and 41 respectively, have been deposited as *E.coli* (PTE 255-22), *E.coli* (PTE 255-28) and *E.coli* (PTE 255-41) at the American Type Culture Center as ATCC 67542, ATCC 67543 and ATCC 67544.

The following experimental examples are illustrative and non limiting of the invention.

EXAMPLE 1

Identification of the S1 subunit region correlated to the ADP-ribosylation activity.

A. Construction of the hybrid plasmids containing the gene coding for modified S1 by deletion of the 3' terminal part.

10 μg of the PTE 255 plasmid are suspended in 100 μl of buffer solution (50 mM Tris-HCl, pH 7.4, 10 mM $MgCl_2$, 100 mM NaCl) and digested at 37° C. for two hours with 30 units (U) of XbaI (BRL) restriction enzyme and then aliquots of 10 μl of the digestion mixture are treated with 3U of one of the following enzymes: NcoI, BalI, NruI, SalI and SphI at 37° C. for two more hours.

The DNA mixtures so digested containing the 75 base pairs (bp) XbaI-NcoI, 377 bp XbaI-BalI, 165 bp XbaI-NruI, 355 bp XbaI-SalI and 503 bp XbaI-SphI fragments respectively, were added with 3 U of Klenow polymerase large fragment and with 2 μl of a solution containing 50 mM of each of the following desoxynucleotides dATP, dTTP, dCTP and dGTP to repair the molecules ends.

The mixtures are maintained at ambient temperature (20–25° C.) for 15 minutes and at 65° C. for further 30 minutes in such a way as to inactivate the polymerase enzyme.

At the end of said period, the mixtures are diluted to 200 μL with ligase buffer (66 mM Tris-HCl, pH 7.6, 1 mM ATP, 10 mM $MgCl_2$, 10 mM Dithiothreitol) and are maintained at 15° C. for one night in the presence of one unit of T4 DNA ligase so that the DNA molecules which Lost the above mentioned fragments are linked again to each other. The ligase mixtures are then employed to transform K12-Hl trp *E.coli* cells prepared by a treatment with 50 mM $CaCl_2$ (Mandel M. & Higa (1970) I. Mol. Biol. 53, 154).

The transformants were selected by plating the cells on LB agar (10 g/l Bacto Tryptone (DIFCO), 5 g/l Bacto Yeast extract (DIFCO) 5 g/l NaCl) medium containing 30 μg/ml ampicillin and incubating the plaques at 30° C. for 18 hours. The recombinant plasmids are analyzed in order to verify the exact nucleotide sequence.

The following hybrid plasmids have been therefore identified:

PTE NCO in which the S1 gene lacks of the part coding for the carboxyterminal sequence of the S1 subunit comprised between the aminoacids 255 and 211.

PTE NRU where the S1 gene lacks of the part coding for the carboxyterminal sequence of the S1 subunit comprised between the aminoacids 255 and 180.

PTE BAL where the S1 gene is lacking of the part which codes for the carboxyterminal sequence of the S1 subunit from 255 to 124.

PTE SAL: in which the S1 gene is Lacking of the part coding for the carboxyterminal sequence of the S1 subunit comprised between the aminoacids 255 and 110.

PTE SPH: in which the S1 gene is lacking of the part coding for the carboxyterminal sequence of the S1 subunit comprised between the aminoacids 255 and 68.

B. Construction of hybrid plasmids containing the gene coding for modified S1 by deletion of the 5' terminal part 3 probes (10 μg) of the PTE 255 plasmid were digested in 100μl of a buffer solution (50 mM Tris-HCl, pH 7.4, 10 mM $MgCl_2$, 50 mM NaCl) at 37° C. for 3 hours, with 30 U of each of the following restriction enzymes SphI, SalI and BalI respectively.

3 U of Klenow large fragment polymerase enzyme are then added to each solution together with 2 μl of a solution containing 50 mM of each of the following desoxynucleotides: dATP, dTTP, dCTP and dGTP and after 15 minutes at 20–25° C. the enzyme is inactivated at 65° C. for 30 minutes.

30 U of HindIII restriction enzyme are then added to each solution and the resulting mixtures are maintained at 37° C. for 3 hours and then loaded on 1.5% agarose gel at 70 Volts for 3.5 hours. In this way two bands are separated for each mixture, one containing the deletion part of S1 and the other containing the PeX-34 plasmid and part of S1.

The 520 bp Sph-Hind III, 372 bp SalI-Hind III and 394 bp BalI-HindIII fragments are then electroeluted by the Maniatis method (Molecular Cloning: a laboratory Manual, Cold Spring Harbor, 1982). 100 ng of each of said fragments are then Linked, in 30 μl of ligase mixture in the presence of 1 U T4 DNA Ligase, with the plasmid Pex-34 previously digested with the BamHI restriction enzyme, treated with the polymerase enzyme and the solution of desoxynucleotides and then digested with the HindIII restriction enzyme.

The ligase mixtures are successively employed to transform *E.coli* K12,ΔHl, Δtrp cells and the transformants are selected on LB agar medium containing ampicillin as reported in point A.

Among the plasmids extracted from the positive clones, those containing in a proper frame the cloned fragments have been identified by Western-blot with pertussis antitoxin antibodies.

Said plasmids, labeled with the abbreviations PTE SPH/HIND, PTE 255/SAL and PTE 255/BAL are Lacking of the S1 gene sequences which code for aminoterminal parts of the subunit comprised between the aminoacids:

1–67, 1–109 and 1–123 respectively.

C. Construction of hybrid plasmids containing the gene coding for modified S1 by deletion of 3' and 5' terminal parts 2 samples (10 μg) of the plasmid PTE NCO (obtained as illustrated in step A) are digested in 100 μl of 50 mM Tris-HCl, pH 7.4, 10 mM $MgCl_2$, 50 mM NaCl solution, with 30 U of BstN1 (BRL) and 30 U of BalI (BRL) respectively, at 37° C. for 3 hours.

The digestion mixtures are then treated at 20–25° C. for 15 minutes with 3 U of Klenow polymerase enzyme in the presence of 2 mM of dATP, dGTP, dCTP and dTTP to complete the terminal portions and, after inactivation of the enzyme at 65° C. for 30 minutes, the DNA are again cut with 30 U of HindIII restriction enzyme at 37° C. for 3 hours.

The digestion mixtures are loaded on 1.5% agarose gel and eluted at 70 Volts for 3.5 hours, the 527 bp BstN1-HindIII and the 279 bp BalI-HindIII fragments being electro-eluted as reported above.

100 ng of said fragments are subsequently linked to the plasmid PeX-34 (previously treated as reported in B) in a ligase mixture in the presence of 7 U T4 DNA ligase at 15° C. for 18 hours. The transformation of the *E. coli* cells and the selection of the transformants is then performed as illustrated above. The fragments inserted in the right frame have been identified among the recombinant plasmids extracted from the positive clones.

Said plasmids, labeled with the abbreviation PTE 34A and PTE NCO/BAL contain respectively the S1 gene without the sequences coding for the S1 subunit parts comprised between the aminoacids 1–52 and 255–211 and for the parts 1–124 and 255–211.

D. Construction of PTE 16-A and 18-A plasmids

10 $\mu$g of the PTE 255 plasmid are digested in 100 $\mu$l of 100 mM Tris-HCl, 50 mM NaCl, 10 mM $MgSO_4$ buffer with 30 U of EcoRI and then with 1 U of Bal31 (BRL) in 10 mM $CaCl_2$, 10 mM $MgCl_2$, 0.2 M NaCl, 20 mM Tris-HCl, pH 8, 1 mM EDTA at 37° C. Mixture aliquots are withdrawn after 1, 3, 5 and 10 minutes and the deletion fragments at the 5' terminal are then cut with HindIII, purified by gel electrophoresis and, after elution, linked to the Pex-34 plasmid as reported above. The ligase mixtures are then employed to transform the *E.coli* cells and the transformants are selected operating as reported in the preceding steps.

The plasmids containing the S1 gene fragments inserted in the right frame, detached by their nucleotide sequence analysis, are isolated from the plasmids extracted from the positive clones.

The plasmids containing the S1 gene without the sequence which codes for the S1 aminoterminal part are selected from the plasmids so obtained.

In particular, the PTE 16-A plasmid lacks of the nucleotides coding for the first 10 aminoacids and therefore codes a protein containing the 11–235 aminoacids, whereas the PTE 18-A plasmid codes for a protein containing the 149–235 aminoacids.

EXAMPLE 2

Expression of the modified S1 subunits and determination of the ADP-ribosylation activity thereof A. K12, ΔHL, Δtrp *E.coli* cells, transformed with the plasmids prepared as reported in the preceding example 1, are cultivated in 20 ml of liquid LB medium under smooth mixing at 30° C. for one night.

10 ml of each culture are employed to inoculate 400 ml of LB medium and are cultivated at 30° C. for 2 hours and at 42° C. for 2.5 hours.

At the end of said period, the culture are centrifuged at 10,000 revolutions per 15 minutes at 4° C., the supernatants discarded, the cells recovered and then resuspended in 3.2 ml of 2.5% saccharose, 10 mM Tris-HCl (pH 8.0), 1 mM EDTA solution.

0.1 ml of a lysozyme solution (40 mg/ml) and 0.8 ml of 0.5 M EDTA were added to the solutions which is then reacted at 37° C. for 30 minutes.

8 ml of a lysis buffer (1% Triton-X 100, 50 mM Tris-HCl, pH 6.0, 63 mM EDTA) are then added to each solution which is maintained at 0° C. for 15 minutes and at 37° C. for 30 minutes.

After a 1 minute sonication the mixtures containing the lysed cells and the parts included, are centrifuged at 10,000 revolution per 10 minutes, the supernatants are discarded and the precipitates resuspended in 5 ml of 1 M urea and maintained at 37° C. for 30 minutes.

The mixtures are again centrifuged and the precipitates or included parts are recovered and dissolved in 5 ml of phosphate buffer saline (PBS) and stocked at −20° C.

B. Analysis of the ADP-ribosylation activity

The solutions containing the included parts are centrifuged and the precipitates resuspended in 100 $\mu$l of 8 M urea before performing the ADP-ribosylation test.

The ADP-ribosylation test is performed according to the technique described by Manning et al. (1984). (J. Biol. Chem. 259, 749–756).

In practice, 10 $\mu$l of each solution are preincubated with a 20 $\mu$l solution of 100 mM of dithiothreitol at 20–25° C. for 30 minutes and then added to 10 $\mu$l of ox retina homogenate (ROS), 80 $\mu$l of water, 5 $\mu$l Tris-HCl (pH 7.5), 1 $\mu$l of an 100 mM ATP solution, 1 $\mu$l of 10 mM GTP solution, 10 ml of thymidine and 1 $\mu$l (1 nCi) $^{32}$PNAD.

The mixtures are then reacted at ambient temperature (20–25° C.) for 30 minutes and, after centrifugation, the residues containing the ROS are recovered and dissolved in 30 $\mu$l of sodium dodecyl-sulphate (SDS) buffer and loaded on 12.5% polyacrylamide gel. After electrophoresis at 25 mA for 4 hours, the gels are vacuum-dried at a temperature of 80° C. and then submitted to autoradiography. The radio-active bands are separated from the gel, suspended in 5 ml of liquid scintillation cocktail (Econofluor, NEN) and counted by a beta counter.

This way the ADP-ribosylation of the modified proteins is quantitatively determined.

The results obtained are reported in the following table I:

| Plasmids containing the modified S1 gene | APD-ribosylation activity of the modified S1 (%) |
|---|---|
| PTE NCO | 100 |
| PTE NRU | 60 |
| PTE BAL | — |
| PTE SAL | — |
| PTE SPH | — |
| PTE 16-A | — |
| PTE 34-A | — |
| SPH/HIND | — |
| 255/BAL | — |
| 255/SAL | — |
| NCO/BAL | — |
| 18-A | — |

Its clearly apparent from what is disclosed in the table, that the sequences following the Nru site (179 position) are not necessary, contrary to the 5' terminal sequences, for the ADP-ribosilation activity of the S1 subunit.

EXAMPLE 3

Identification and mutation of the active sites of the 1–180-region of the S1 subunit 10 $\mu$g of the PTE 255 plasmid are suspended in 100 $\mu$l of 10 mM Tris-HCl, pH 7.5, 50 mM NaCl, 10 mM $MgCl_2$ buffer and digested with 30 U of each of the EcoRI and Hind-III enzymes at 37° C. for 3 hours.

The digestion mixture is then loaded on a 1.3% agarose gel and eluted at 80 mA for 3 hours.

Operating in this way two bands are separated; one of 3,500 bp containing the vector and the other of 600 bp containing the gene which codes for the S1 subunits.

The bp band is then electro-eluted and 0.2 $\mu$g of the fragment and 0.3 ng of the Bluescript SK (Stratagene, San Diego, Calif.) plasmid, previously digested with the EcoRI and HindIII restriction enzymes, are suspended in 20 $\mu$l of buffer solution (66 mM Tris-HCl, pH 7.5, 1 mM ATP, 10 mM $MgCl_2$, 10 mM dithiothreitol) and linked together in the presence of 1 U $T_4$ DNA ligase at 15° C. for 18 hours.

The ligase mixture is then employed to transform the JM 101 *E.coli* cells made suitable and the transformants are selected on plaques of LB agar including 100 μg/ml ampicillin, 20 μg/ml IPTG (isopropyl-B-D-thiogalactopyranoside) and 20 μg/ml X-Gal (5-bromo-4-chloro-3-indolyl-D-galactopyranoside).

The plaques are incubated at 37° C. in thermostatic chamber for 18 hours. The white cultures containing the hybrid plasmid comprising the Bluescript SK vector and the 600 bp DNA fragment are used to isolate the single helix DNA of the cloned fragment operating as follows.

The white cells are cultivated in 1.5 ml LB liquid medium in order to reach an optical density, (OD) at 590 mm of about 0.15.

10 μl of a F1 phage (Stratagene San Diego, Calif.) suspension in LB ($5\times10^{12}$ phages/ml) are subsequently added to the cultures and the resulting solutions are maintained at 37° C. for 6–8 hours.

At the end of said period, the cells are separated from the culture medium by centrifugation and the supernatant is recovered. A 20% polyethylenglycol (PEG) and 2.5 mM NaCl were added to 1 ml of said supernatant to precipitate the phages.

After 15 minutes at ambient temperature (20–25° C.), the mixture is centrifuged at 12,000 g for 5 minutes in an Eppendorf centrifuge at 20° C. and the phages so recovered are resuspended in 100 μl TE (10 mM Tris-HCl, pH 7.5, 1 mM EDTA) buffer.

The solution is then extracted once with one volume of water-saturated phenol, twice with ethyl ether and finally, the single helix DNA is precipitated adding to the aqueous phase 250 μl of ethanol and 10 μl of 3 M ammonium acetate. The DNA is separated from the mixture by centrifugation, is resuspended in 20 μl of TE buffer and is employed for the direct site mutagenesis (Zoller et al. DNA, 3, 479–488, 1984).

To this end, oligonucleotides in which the bases which code for at least one of the desired aminoacids are modified in order to code for another aminoacid, are synthesized by means of a 1 Plus DNA synthesizer System (Beckman) automatic system.

Said oligonucleotides, complementary of the sequence present in the single helix DNA cloned in the Bluescript SK plasmid, are used as primers for the DNA polymerase which transcribes the whole Bluescript nucleotidic sequence incorporating the mutations present in the primer.

In practice, 2 μl of 10 mM ATP, 2 μl of Kinase 10 X (550 mM Tris-HCl, pH 8.0, 100 mM $MgCl_2$) buffer, 1 μl of 100 mM dithiothreitol (DTT) and 5 U of polynucleotide Kinase (Boehringer) are added to 3 mM of the synthetic oligonucleotide and the final volume is brought to a value of 20 μl.

The mixture is incubated at 37° C. for 30 minutes and the enzyme is inactivated at 70° C. for 10 minutes.

1 μg of the single filament used as matrix, 1 μl of 1 mM Tris-HCl, pH 8.0, and 10 mM $MgCl_2$ in 1 volume of 10 X Kinase buffer, are added to 2 μl of the primer.

The mixture is maintained at 80° C. for about 3 minutes and then at ambient temperature for about 1 hour.

10 μl of 1 mM Tris-HCl, pH 8.0, 10 mM $MgCl_2$ buffer, 0.05 mM ATP, 1 mM DTT, 0.5 mM of the four desoxynucleotides, 1 U of T4 DNA ligase and 2.5 U of I DNA polymerase (Klenow fragment) are subsequently added.

The mixture is incubated at 15° C. for one night and then used to transform JM 101 *E.coli* cells as illustrated above.

The plasmid containing the mutated S1 gene are then identified by the hybridization technique using as probe the primer used for the mutagenesis, marked with $^{32}P$. In practice, the nitrocellulose filters containing the transformed cultures are hybridized in 6×SSC (1×SSC=0.015 M NaCl, 0.015M trisodium citrate, pH7), 10×Denhardt (1% BSA, 1% Ficoll, 1% polyvinyl-pyrrolidone) and 0.2% Sodium-dodecylsulphate (SDS) at 20–25° C. for 18 hours and then washed for 2 hours in 6×SSC at the following temperatures: (45° C.) 25 and 26 mutants; (48° C.) 28, 22 and 29 mutants; (54° C.) 27; (46° C.) 31 and 41 mutants.

The mutations are confirmed by analysis of the nucleotide sequence of the gene according to the method of Sanger, F. et al. (PNAS 74, 5463, 1977).

Operating as reported above, plasmids containing the gene coding for S1 modified are prepared as follows:

41: 8 Tyrosine and 9 arginine are substituted with Aspartic acid and Glycine respectively, using the GTCATAGCCGTCTACGGT primer.

The corresponding gene has been so modified:

620-CGCCACCGTATACCGCTATGACTCCCGCCCG-650

620-CGCCACCGTAGACGGCTATGACTCCCGCCCG-650

22: 50 phenylalanine and 53 threonine are substituted with glutamic acid and isoleucine respectively, using the TGGAGACGTCAGCGCTGT primer.

The corresponding gene has been so modified:

The 750-AGCGCTTTCGTCTCCACCAGC-770 sequence has been changed into 750-AGCGCTGACGTCTCCATCAGC-770.

25: 99 glycine has been substituted with glutamic acid using the CTGGCGGCTTCGTAGAAA primer.

The corresponding gene has been so modified:

the 910-TACGGCGCCGC-920 sequence has been changed into910-TACGAAGCCGC-920.

17: 109 aspartic acid has been substituted with glycine using the CTGGTAGGTGTCCAGCGCGCC primer.

The corresponding gene has been so modified:

the 930-GTCGACACTTA-940 sequence has been changed into 930-GTCGGCACTTA-940.

27: 121 glycine has been substituted by glutamic acid using the GCCAGCGCTTCGGCGAGG primer.

The corresponding gene has been so modified:

the 956-GCCGGCGCGCT-966 sequence has been changed into 956-GCCGAAGCGCT-966.

16: Alanine in position 124 has been substituted with aspartic acid using the GCCATAAGTGCCGACGTATTC primer.

The corresponding gene has been so modified:

the 976-TGGCCACCTAC-984 sequence has been changed into 976-TGGACACCTAC-986.

1716: contains the combined 16 and 17 mutations.

28: 129 glutamic acid has been substituted in glycine using the GCCAGATACCCGCTCTGG primer.

The corresponding gene has been so modified:

the 990-AGCGAATATCT-1000 sequence has been changed into 990-AGCGGGTATCT-1000.

29: 135 arginine has been substituted with the glutamic acid using the GCGGAATGTCCCGGTGTG primer.

The corresponding gene has been so modified:

the 1010-GCGCATTCCGC-1020 sequence has been changed into 1010-GGACATTCCGC-1020.

31: 159 threonine has been substituted with lysine using the TACTCCGTTTTCGTGGTC primer.

The corresponding gene has been so modified:

1070-GCATCACCGGCGAGACCACGACCACGGAGTA-1090 has been changed into 1070-GCATCACCGGCGAGACCACGAAAACGGAGTA-1090.

26: 111 tyrosine is substituted with glycine.

Furthermore, owing to a partial duplication of a primer fragment, the insertion of the Asp Thr Gly Gly aminoacids occured in the position 113 using the CGCCACCAGTGTCGACGTATTCGA primer. The corresponding gene has been so modified:

930-GTCGACACTTATGGCGACAAT-950

930-GTCGACACTGGTGGCGACACTGGTGGCGACAAT-950.

The plasmids containing the S1 gene are digested again with the EcoRI and HindIII restriction enzymes and the DNA fragment containing the above mentioned mutations are separated from the digestion mixture by gel electrophoresis, are electro-eluted and cloned in the PEx-34B vector in a ligase mixture operating as reported above.

The ligase mixtures are used to transform suitable K12-Δ HI Δtrp *E.coli* cells and the transformants isolated on LB agar medium containing 30 μg/ml of ampicillin at 30° C.

The positive clones containing the mutated plasmids are then cultivated in LB liquid medium as reported in the preceding example 2 and, after cellular lysis, the ADP-ribosylation activity of the S1 subunits so obtained is determined.

The results are reported in the following table II:

| Mutant subunits | ADP-ribosylation activity of the mutated subunits (%) |
|---|---|
| 41 | 0 |
| 22 | 0 |
| 25 | 100 |
| 17 | 46 |
| 26 | 150 |
| 27 | 43 |
| 16 | 50 |
| 1617 | 23 |
| 28 | 0 |
| 29 | 92 |
| 31 | 100 |
| BppB | 100 |

BppB is an S1 hybrid containing the gene part up to SalI of *B.pertussis* and the remaining of *B. bronchisephica.*

From the results reported above the mutant 28 in which the substitution of only one aminoacid has determined the complete loss of the enzymatic activity, seems particularly interesting.

We claim:

1. A method for the preparation of an immunologically active mutant polypeptide having no or reduced toxicity, which method comprises:

(a) modifying by site-directed mutagensis the DNA of the S1 subunit of the gene in the operon which codes for pertussis toxin by substitution in one or more sites of said S1 subunit the DNA sequence coding for a substitute amino acid for the DNA coding for an amino acid at said site in said S1 subunit:

(b) constructing a hybrid plasmid linking a cloning vector with said DNA of said S1 subunit;

(c) transforming a host microorganism with said hybrid plasmid;

(d) cultivating said transformed microorganism in a suitable culture medium; and (e) recovering said mutant polypeptide produced by said microorganism;

said substitution comprising said substitute amino acids being selected from the group consisting of:

(1) glutamic acid at position 129 substituted by glycine at position 129;

(2) tyrosine at position 8 and arginine at position 9 substituted by aspartic acid at position 8 and glycine at position 9; and (3) phenylalanine at position 50 and threonine at position 53 substituted by glutamic acid at position 50 and isolucine at position 53.

2. The method of claim 1 wherein wherein said substitute amino acids comprise glutamic acid at position 129 substituted by glycine at position 129.

3. The method of claim 1 wherein wherein said substitute amino acids comprise tyrosine at position 8 and arginine at position 9 substituted by aspartic acid at position 8 and glycine at position 9.

4. The method of claim 1 wherein wherein said substitute amino acids comprise phenylalanine at position 50 and threonine at position 53 substituted by glutamic acid at position 50 and isolucine at position 53.

5. The method of claim 1 wherein said mutant polypeptide exhibits a complete loss of ADP-ribosylation activity as compared with natural pertussis toxin.

* * * * *